United States Patent [19]
Jimbo et al.

[11] Patent Number: 6,160,044
[45] Date of Patent: Dec. 12, 2000

[54] COMPOSITIONS CONTAINING DITHIOCARBONATE COMPOUND

[75] Inventors: Shinichiro Jimbo; Shoshiro Matsushita, both of Tokyo; Ikuo Shimizu, Yokkaichi; Iwao Hotta, Yokkaichi; Masanori Ikuta, Yokkaichi; Izumi Itani, Yokkaichi, all of Japan

[73] Assignee: Kyowa Yuka Co., Ltd., Tokyo, Japan

[21] Appl. No.: 09/402,124

[22] PCT Filed: Apr. 2, 1998

[86] PCT No.: PCT/JP98/01514

§ 371 Date: Sep. 30, 1999

§ 102(e) Date: Sep. 30, 1999

[87] PCT Pub. No.: WO98/45373

PCT Pub. Date: Oct. 15, 1998

[30] Foreign Application Priority Data

Apr. 4, 1997 [JP] Japan ..................................... 9-086218

[51] Int. Cl.$^7$ ............................... C08K 5/04; C08K 5/09; C08K 3/10
[52] U.S. Cl. .......................... 524/241; 524/251; 524/394; 524/398; 524/403; 524/406; 524/408; 524/413; 524/431; 524/432; 524/434; 524/435; 428/500
[58] Field of Search .................................. 524/241, 251, 524/394, 398, 403, 406, 408, 413, 431, 432, 434, 435; 428/500

[56] References Cited

FOREIGN PATENT DOCUMENTS

| | | |
|---|---|---|
| 5-247027 | 9/1993 | Japan . |
| 7-62190 | 3/1995 | Japan . |
| 7-145164 | 6/1995 | Japan . |
| 8-217774 | 8/1996 | Japan . |
| 9-59324 | 3/1997 | Japan . |

OTHER PUBLICATIONS

Derwent Patent Abstracts of JP 09059324, Mar. 4, 1997, Derwent Acc. No. 1997–209359, Sep. 1997.

Journal of Polymer Science: Part A: Polymer Chemistry, vol. 33, pp. 1005–1010, May 1995.

Primary Examiner—Kriellion Sanders
Attorney, Agent, or Firm—Fitzpatrick, Cella, Harper & Scinto

[57] ABSTRACT

The present invention provides a composition comprising a polymer or a compound having at least one 5-membered ring dithiocarbonate group represented by general formula (I):

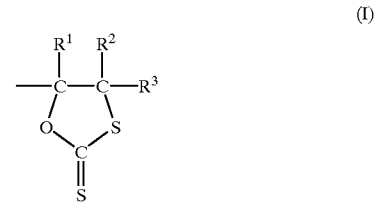

(wherein $R^1$, $R^2$, and $R^3$ are the same or different and each of which represents hydrogen or lower alkyl), a nucleophile, and a metal compound.

22 Claims, No Drawings

COMPOSITIONS CONTAINING DITHIOCARBONATE COMPOUND

TECHNICAL FIELD

The present invention relates to compositions comprising a compound having at least one 5-membered ring dithiocarbonate group which are useful in applications such as coatings, adhesives, inks, sealing agents or the like.

BACKGROUND ART

A reactive polymer or compound which has a functional group in its molecule is useful in various applications. For example, if a composition comprising such a polymer or a compound is used as an active ingredient for a coating, an adhesive, an ink, a sealing agent for building use, a sealant for semiconductors or the like, such physical properties as hardness, strength, adhesion, water resistance, chemical resistance, heat resistance, or the like can be improved by allowing cross-linking reactions to occur under specific conditions after coating or printing of the composition.

As the reactive polymer or compound which has a functional group in its molecule, for example, polymers or compounds having a 5-membered ring dithiocarbonate group are known.

As a polymer having 5-membered ring dithiocarbonate groups, for example, Japanese Unexamined Patent Application, First Publication No. Hei 5-247027 discloses a homopolymer of 5-(methacryloyl)methyl-1,3-oxathiolane-2-thione (MOT).

In addition, Journal of Polymer Science, Part A: Polymer Chemistry 33, 1005 (1995) discloses a composition comprising a vinyl copolymer having 5-membered ring dithiocarbonate groups and an amine compound.

In addition, Japanese Unexamined Patent Application, First Publication No. Hei 5-247027 and Japanese Unexamined Patent Application, First Publication No. Hei 7-145164 disclose compositions comprising a compound having 5-membered ring dithiocarbonate groups and a nucleophile or a polymer having functional groups containing active hydrogens.

In addition, Japanese Unexamined Patent Application, First Publication No. Hei 7-62190 discloses a composition comprising a compound having two or more amino groups and imino groups and an aqueous dispersion liquid of a vinyl copolymer having 5-membered ring dithiocarbonate groups.

In addition, Japanese Unexamined Patent Application, First Publication No. Hei 8-302010 and Japanese Unexamined Patent Application, First Publication No. Hei 8-302012 disclose polythiourethane formed from a compound having 5-membered ring dithiocarbonate groups and alkanediamine or xylylenediamine.

It is known that with compounds having 5-membered dithiocarbonate groups as mentioned above, the dithiocarbonate groups undergo a ring opening addition reaction with nucleophiles, furthermore, the thiol groups generated in this reaction are oxidized by air, and disulfide bonds are generated, giving rise to the formation of a highly-ordered cross-linked structure.

However, when compounds or polymers having 5-membered ring dithiocarbonate groups are used in applications such as coatings, adhesives, or the like, there is a problem that the rate of the air oxidation reaction of the thiol groups is slow, and it is necessary to promote the air oxidation reaction of these thiol groups, and to increase the rate of generation of the disulfide bonds.

DISCLOSURE OF INVENTION

The present invention provides a composition comprising a compound having at least one 5-membered ring dithiocarbonate group represented by general formula (I):

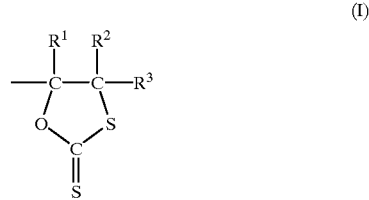

(in general formula (I), $R^1$, $R^2$, and $R^3$ are the same or different and each of which represents hydrogen or lower alkyl), a nucleophile and a metal compound.

BEST MODE FOR CARRYING OUT THE INVENTION

In the above-mentioned general formulae (I), $R^1$ is hydrogen or a lower alkyl group. Here, a lower alkyl group includes straight or branched alkyl groups having 1 to 4 carbon atoms, such as a methyl group, ethyl group, propyl group, isopropyl group, butyl group, isobutyl group, and tert-butyl group.

In the present invention, the compound having at least one 5-membered ring dithiocarbonate group may be a polymer.

Examples of the polymer having at least one 5-membered ring dithiocarbonate group represented by general formula (I) are a vinyl polymer, a polyester resin, an alkyd resin, a polyamide resin, a polyether resin, a polyurethane resin, and a copolymer in which these resins are chemically bonded to each other, and among these, vinyl copolymers are preferable.

Among vinyl polymers, vinyl copolymers containing a structural unit represented by general formula (II)

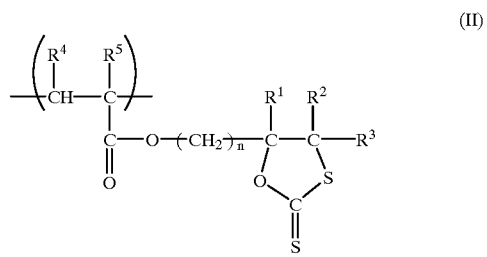

(in general formula (II), $R^1$, $R^2$, and $R^3$ are the same or different and each of which represents hydrogen or lower alkyl; $R^4$ and $R^5$ are the same or different and each of which represents hydrogen, methyl, or ethyl; and n represents an integer of 1 to 4) are more preferable due to the ease of obtaining monomers, and the like.

The vinyl copolymer having at least one 5-membered ring dithiocarbonate group comprises a structural unit having a 5-membered ring dithiocarbonate group and preferably 1 to 10 types of structural units other than the structural unit having a 5-membered ring dithiocarbonate group.

For the vinyl copolymer containing at least one 5-membered ring dithiocarbonate group, examples of the monomer which is copolymerized with the monomer having at least one 5-membered ring dithiocarbonate group include (meth)acrylic acid, maleic acid, fumaric acid, itaconic acid, crotonic acid, monoethyl maleate, monomethyl itaconate, methyl (meth)acrylate, ethyl (meth)acrylate, butyl (meth)acrylate, isobutyl (meth)acrylate, t-butyl (meth)acrylate, 2-ethylhexyl (meth)acrylate, lauryl (meth)acrylate, styrene, vinyltoluene, α-methylstyrene, dimethylstyrene, divinylbenzene, n-methylol(meth)acrylamide, (meth)acrylamide, (meth)acrylonitrile, vinyl acetate, vinyl propionate, vinyl versate, monoethyl maleate, monobutyl maleate, diethyl maleate, dibutyl maleate, diethyl fumarate, dibutyl fumarate, diethyl itaconate, 2-hydroxyethyl (meth)acrylate, 2-hydroxypropyl (meth)acrylate, polyethylene glycol mono(meth)acrylate, polypropylene glycol mono(meth)acrylate, dimethylaminoethyl (meth)acrylate, glycidyl (meth)acrylate, dimethylaminoethyl (meth)acrylate, diethylaminoethyl (meth)acrylate, (meth)acrylamide, methyl vinyl ether, ethyl vinyl ether, butyl vinyl ether, allyl alcohol, allyl alcohol ester, vinyl chloride, vinylidene chloride, fluoroethylene, chlorofluoroethylene, and butadiene. Among these compounds, acrylic acid or methacrylic acid or a lower alkyl ester thereof, such as (meth)acrylic acid, methyl (meth)acrylate, ethyl (meth)acrylate, butyl (meth)acrylate, isobutyl (meth)acrylate, and t-butyl (meth)acrylate, can be preferably used. Alternatively, a copolymer of a vinyl compound and a non-vinyl compound can be used, and examples thereof include a vinyl-modified epoxy resin (Japanese Unexamined Patent Application, First Publication No. Sho 54-30249), a vinyl-modified polyester resin (Japanese Unexamined Patent Application, First Publication No. Hei 1-129072), a vinyl-modified alkyd resin, and a vinyl-modified urethane resin (Japanese Unexamined Patent Application, First Publication No. Hei 1-301761).

In the polymer having at least one 5-membered ring dithiocarbonate group, the content of the structural unit having a 5-membered ring dithiocarbonate group (based on monomer) is preferably 0.2 to 90 mol %. If the content of the structural unit having a 5-membered ring dithiocarbonate group is less than 0.2%, when used in applications such as coatings, the impact resistance, and the hardness of the coating film obtained therefrom is inferior and if it exceeds 90%, the flexibility is inferior. Therefore, these situations are undesirable.

The molecular weight of the polymer having at least one 5-membered ring dithiocarbonate group is not particularly limited; however, when the polymer is used for an oil soluble coating, one having a weight-average molecular weight (Mw) of 1,000 to 400,000 can be used, and particularly one having a weight-average molecular weight of 5,000 to 200,000 can be preferably used.

Processes for producing the polymer having at least one 5-membered ring dithiocarbonate group will be explained in the following.

The polymer having at least one 5-membered ring dithiocarbonate group can be obtained by conducting polymerization/polycondensation with a corresponding monomer according to a known method. The monomer having at least one 5-membered ring dithiocarbonate group can be obtained by allowing an oxirane compound and carbon disulfide to react in the presence of an alkali halide, such as lithium bromide, in accordance with, for example, a known method described in Japanese Unexamined Patent Application, First Publication No. Hei 5-247027 or the Journal of Organic Chemistry (J. Org. Chem.), 60, 473 (1995).

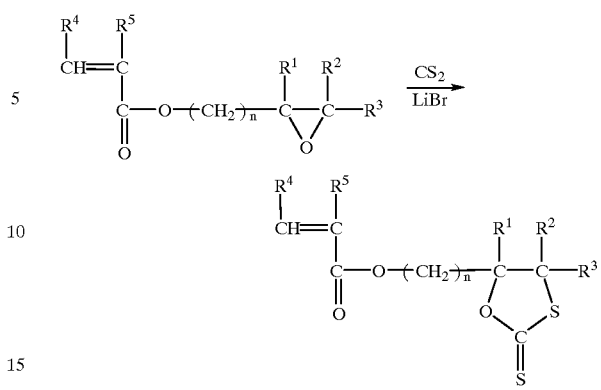

(In the formula, $R^1$, $R^2$ and $R^3$ are the same or different and each of which represents hydrogen or lower alkyl; $R^4$ and $R^5$ are the same or different and each of which represents hydrogen, methyl or ethyl; and n represents an integer of 1 to 4.)

Alternatively, the polymer having at least one 5-membered ring dithiocarbonate group within its molecule (hereinafter referred to as copolymer) can also be produced by obtaining a polymer having a functional group (such as a carboxyl group, a hydroxyl group, or an amino group) in advance using a known method, and then allowing a bonding reaction to occur with a 5-membered ring dithiocarbonate compound so that it becomes pendent from the polymer.

Examples of processes for producing a copolymer include a process in which a monomer having a 5-membered ring dithiocarbonate group in its molecule and another copolymerizable monomer are allowed to undergo copolymerization; a process in which a homopolymer or a copolymer is synthesized, and thereafter it is graft-copolymerized with another monomer; a process in which after synthesis of a copolymer, polymers are block-copolymerized; and the like.

The polymerization reaction is carried out, for example, in the case of radical polymerization of a vinyl monomer, at 0 to 150° C., preferably at 40 to 120° C., for 1 to 24 hours in the presence of a polymerization initiator at 0.5 to 5 mol % with respect to the amount of the monomer.

If an aqueous emulsified vinyl polymer is desired, a monomer can be subjected to emulsion polymerization in water using an emulsifier and a polymerization initiator according to known process (Japanese Unexamined Patent Application, First Publication No. Sho 54-110248, or Japanese Examined Patent Application, Second Publication No. Sho 58-20991).

Storage stability of the polymer having at least one 5-membered ring dithiocarbonate group can be improved by making the polymer have a core-shell structure. An emulsion polymer in water of a core-shell type can be synthesized according to known processes (Japanese Unexamined Patent Application, First Publication No. Sho 57-3850, Japanese Unexamined Patent Application, First Publication No. Sho 61-136501, and Japanese Unexamined Patent Application, First Publication No. Hei 5-70733).

The polymer having at least one 5-membered ring dithiocarbonate group can be emulsified in water according to a known process.

As the solvent for polymerization, although it varies depending on the polymerization type, for example, in the case of radical polymerization, benzene, toluene, xylene, hexane, cyclohexane, ethyl acetate, butyl acetate, 3-methyl-3-methoxybutyl acetate, acetone, methyl ethyl ketone, methyl isobutyl ketone, diisobutyl ketone, cyclohexanone, methanol, ethanol, propanol, isopropanol, butanol, N-methylpyrrolidone, tetrahydrofuran, acetonitrile, methoxybutanol, methoxybutyl acetate, 3-methyl-3-methoxybutanol, ethylene glycol monobutyl ether, ethylene glycol monobutyl ether acetate, diethylene glycol monobutyl ether, diethylene glycol monobutyl ether acetate, propylene glycol monomethyl ether, dipropylene glycol monomethyl ether, propylene glycol monoethyl ether, propylene glycol monomethyl ether acetate, dipropylene glycol monomethyl ether acetate, 3-methyl-3-methoxy-1-butyl acetate, water, dimethylformamide, dimethylacetamide, dimethyl sulfoxide or the like can be used.

As the polymerization initiator, although it varies depending on the polymerization type, for example, in the case of radical polymerization, 2,2'-azobisisobutyronitrile, 2,2'-azobis-2-methylbutyronitrile, 2,2'-azobisvaleronitrile, benzoyl peroxide, acetyl peroxide, lauroyl peroxide, 1,1-bis(t-butylperoxy)-3,3,5-trimethylcyclohexane, t-butyl peroxy-2-ethylhexanoate, cumene hydroperoxide, t-butyl peroxybenzoate, t-butyl peroxide, methyl ethyl ketone peroxide, m-chloroperbenzoic acid or the like can be used.

As the emulsifier for aqueous emulsion polymerization, an anionic emulsifier such as an alkylbenzenesulfonate salt, a nonionic emulsifier such as polyethylene glycol alkylphenyl ether, a reactive emulsifier such as "ELEMINOL JS-2" (a product of Sanyo Chemical Industries, Ltd.), a polymer emulsifier in which a hydrophilic group such as a salt of a carboxyl group, a salt of a sulfo group, or the like is introduced into a polymer of various types, such as a vinyl polymer or a polyester polymer, or the like, can be used. In addition, one of various protective colloids for stabilizing emulsification such as polyvinyl alcohol or a cellulose compound can be incorporated.

In order to obtain an aqueous emulsion dispersion composition by a method other than aqueous emulsion polymerization, a self-emulsification method in which a tertiary amine salt of a carboxyl group introduced into the molecule of copolymer, or an emulsification method in which an external emulsifier is used may be employed.

Instead of the above production methods, the polymer of the present invention can also be obtained by allowing a polymer having an oxirane structure to react with carbon disulfide in the presence of an alkali halide such as lithium bromide in accordance with the known method described above (Japanese Unexamined Patent Application, First Publication No. Hei 5-247027; the Journal of Organic Chemistry (J. Org. Chem.), 60, 473 (1995)).

In order to chemically bond the vinyl polymer to the polyester resin, a method in which a vinyl polymer having a functional group such as a carboxyl group, a hydroxyl group, or a glycidyl group and a polyester resin having a glycidyl group, a hydroxyl group, a carboxyl group, or the like, are synthesized in advance, and thereafter the vinyl polymer and the polyester resin are bonded by esterification (Japanese Unexamined Patent Application, First Publication No. Hei 1-129072), or a method in which an unsaturated polyester resin having a radical polymerizable functional group (a vinyl group, a conjugated double bond or the like) is synthesized, and thereafter a vinyl monomer is grafted thereto by radical polymerization may be employed.

Examples of the compound having at least one 5-membered ring dithiocarbonate group according to the present invention include a dithiocarbonate compound derived from phenol, a dithiocarbonate compound derived from a polyhydric alcohol, a dithiocarbonate compound derived from a polycarboxylic acid, and a compound obtained by allowing an oxirane compound such as diphenyl epoxy resin, ethylene oxide, propylene oxide, butylene oxide, triglycidyl isocyanurate, epoxidated soybean oil, or an epoxidated fatty acid of soybean oil to react with carbon disulfide, in addition to the above-described polymers. In particular, a hydroxy compound having a dithiocarbonate group represented by general formula (III):

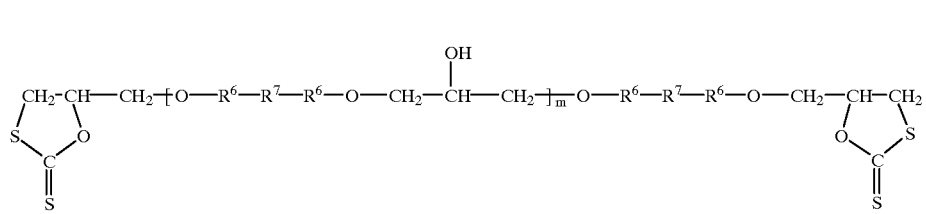

(III)

(in the general formula (III), $R^6$ represents phenylene in which 1 to 4 hydrogen atoms may be substituted by Br, or cyclohexylene; $R^7$ represents methylene, $C(CH_3)_2$, or S; and m represents an integer of 1 to 40) can be preferably used for the reason that when used in applications such as coatings, the coating film obtained therefrom has a combination of superior hardness, flexibility, adhesiveness, and chemical resistance.

Examples of the dithiocarbonate compound derived from phenol are compounds obtained by preparing a glycidyl ether by allowing a phenol compound, such as resorcinol, hydroquinone, pyrocatechol, bisphenol A, dihydroxy diphenyl methane (bisphenol F), bisphenol S, tetrabromobisphenol A, 4,4-dihydroxy-diphenylcyclohexane, 4,4-dihydroxy-3,3-dimethyldiphenylmethane, 4,4-dihydroxybenzophenone, tris(4-hydroxyphenyl)methane, bis(4-hydroxyphenyl)ether, novolak phenol, novolak cresol, bis(4-hydroxyphenyl)sulfone, bis(3,5-dimethyl-4-hydroxyphenyl)sulfone, or a hydride or halide of one of the above-mentioned compounds, to react with epichlorohydrin, and then allowing the glycidyl ether to react with carbon disulfide.

The dithiocarbonate compound derived from a polyhydric alcohol can be obtained by preparing a glycidyl ether by allowing a polyhydric alcohol, such as ethylene glycol, diethylene glycol, triethylene glycol, polyethylene glycol, 1,2-propylene glycol, 1,3-propylene glycol, polypropylene glycol, 1,3-butanediol, 1,4-butanediol, 1,2-butanediol, 1,5-pentanediol, 1,6-hexanediol, neopentylglycol, cyclohexanedimethanol, 3-methyl-1,5-pentanediol, 2,4-diethyl-1,5-pentanediol, 1,9-nonanediol, 1,3-octanediol, trimethylolpropane, trimethylolethane, or glycerine, to react with epichlorohydrin, and then allowing the glycidyl ether to react with carbon disulfide.

Examples of the dithiocarbonate compound derived from a polycarboxylic acid are compounds obtained by preparing a glycidyl compound by allowing a polycarboxylic acid, such as dimer acids synthesized from oxalic acid, succinic acid, glutaric acid, adipic acid, sebacic acid, phthalic acid, hexahydrophthalic acid, 2,6-naphthalene dicarboxylic acid, cyclohexane dicarboxylic acid, or oleic acid; or trimellitic acid, to react with epichlorohydrin, and then allowing the glycidyl compound to react with carbon disulfide.

A compound having at least one 5-membered ring dithiocarbonate group can be obtained by allowing an oxirane compound, which corresponds to the intended product, and carbon disulfide to react in the presence of an alkali halide such as lithium bromide in accordance with the known method described above (Japanese Unexamined Patent Application, First Publication No. Hei 5-247027 or the Journal of Organic Chemistry (J. Org. Chem.), 60, 473 (1995)).

For example, a hydroxy compound represented by general formula (III) can be obtained by allowing a commercially available epoxy resin ("E-1001~1007", manufactured by Yuka Shell Epoxy Kabushiki Kaisha), which corresponds to the hydroxy compound, and carbon disulfide to react in the presence of an alkali halide such as lithium bromide, as mentioned above. Although a commercially available oxirane compound may be used, an oxirane compound may be obtained by allowing a compound having a hydroxyl group and epichlorohydrin to react in the presence of a base in accordance with known methods, if the oxirane compound is not commercially available.

As the nucleophile which is a component of the composition of the present invention, any nucleophile which is capable of a nucleophilic addition reaction with the dithiocarbonyl group of the 5-membered ring dithiocarbonate group is suitable. However, a compound having an amino group, a hydroxy group, an imino group, a thiol group, a phenolic hydroxyl group and the like can be mentioned as examples. Among these, in particular, compounds having an amino group are preferable, and a compound having two or more primary or secondary amino groups within its molecule is even more preferable. The reason why these compounds are preferable is that when used in applications such as coatings, the hardness, impact resistance or the like of the coating film obtained therefrom is superior.

Examples of such amino compounds are lower molecular compounds including monoamines such as methylamine, ethylamine, propylamine, butylamine, hexylamine, octylamine, monoethanolamine, diethanolamine, dimethylamine, diethylamine, diisopropylamine, dibutylamine, and 2-amino-2-methylpropanol; diamines such as ethylenediamine, 1,2-diaminopropane, 1,3-diaminopropane, 1,4-diaminobutane, 1,6-diaminohexane, 1,8-diaminooctane, 1,2-diaminocyclohexane, dimer acid amide, N,N'-bis(2-aminoethyl)ethylenediamine, N,N'-bis(3-aminopropyl)ethylenediamine, and N,N'-dimethyldiaminopropane; triamines such as dicyandiamide, 1,2,3-triaminopropane, 1,2,3-triamino-2-methylpropane, 1,3-diamino-2-aminomethylpropane, 1,2-diamino-2-aminomethylbutane, 1,3-diamino-2-methyl-2-aminomethylpropane, tris(2-aminoethyl)ethane, tris(6-aminohexyl) isocyanurate, 1,3-diamino-2-methylaminopropane, 2-amino-1,3-bis(isopropylamino)-2-methylpropane, and 2-amino-1-isopropylamino-2-isopropylaminomethylbutane; tetramines such as tetrakis(aminomethyl)methane, tetrakis(methylaminomethyl)methane, tetrakis(2-aminoethylaminomethyl)methane, and 1,1,1-tris(2-aminoethylaminomethyl)ethane; polyalkylene polyamines such as diethylenetriamine, triethylenetetramine, tetraethylenepentamine, hexaethyleneoctamine, nonaethylenedecamine, 1,3-bis(2-aminoethylamino)propane, triethylene-bis(trimethylene) hexamine, bis(3-aminopropyl)amine, 1,3-bis(3-aminopropylamino)propane, spermidine, homospermidine, N-(4-aminobutyl)cadaverine, bis(5-aminopentyl)amine, spermine, 1,6-bis(2-aminoethylamino)hexane, and 1,10-bis(2-aminoethylamino)decane; alicyclic amines such as pyrrolidine, piperidine, piperazine, morpholine, and thiomorpholine; basic amino acids such as lysine, ornithine, and arginine; aromatic amines such as aniline and diphenylamine; aralkylamines such as benzylamine; and basic nitrogen-containing heterocyclic compounds such as pyrrole, imidazole, and triazole.

This amino compound is usually used alone, but a mixture of two or more may also be used.

In addition, in the composition of the present invention, in order to control the rate of the reaction between the 5-membered ring dithiocarbonate group and the amino group, a ketimine derivative, an enamine derivative, or an aldimine derivative may be used as the nucleophile. A ketimine derivative, an enamine derivative, or an aldimine derivative can be synthesized from an amino compound having a primary or secondary amino group and a lower molecular carbonyl compound or a lower molecular aldehyde compound in accordance with a known method. A commercially available product such as "H-2" manufactured by Yuka Shell Epoxy Kabushiki Kaisha may also be used.

As the amino compound which is the starting material for the synthesis of the ketimine derivative, the enamine derivative, or the aldimine derivative, the above-mentioned primary or secondary amino compounds can be used.

Examples of the lower molecular carbonyl compound for synthesizing the ketimine derivative or the enamine derivative are ketone compounds such as acetone, methyl ethyl ketone, methyl isobutyl ketone, diisobutyl ketone, and cyclohexanone.

Examples of the lower molecular carbonyl compound for synthesizing aldimine derivative include aldehyde compounds such as acetaldehyde, propionaldehyde, isobutyraldehyde, octylaldehyde, benzaldehyde, α-tolualdehyde, 4-ethylbenzaldehyde, 4-propylbenzaldehyde, 4-butylbenzaldehyde, 2,4-dimethylbenzaldehyde, 2,4,5-trimethylbenzaldehyde, p-anisaldehyde, and p-ethoxybenzaldehyde.

The lower molecular carbonyl compound is normally used in an amount of 0.5 to 5 equivalents, or preferably 0.8 to 1.5 equivalents, to the amino compound. However, use of a greatly excessive amount of the lower molecular carbonyl compound is not objected to, since it can also serve as a solvent.

In the composition according to the present invention, the equivalence ratio of the nucleophile and the 5-membered ring dithiocarbonate group as components is not particularly limited, and when the nucleophile is an amino compound, a ketimine derivative, an enamine derivative, or an aldimine derivative, good coating film properties can be obtained when:

$$\frac{\text{amino groups, imino groups or these groups in which hydrogen has been substituted by alkyl}}{\text{5-membered ring dithiocarbonate groups}}$$

is 0.3 to 2.0, preferably 0.8 to 1.2.

As the metal compound which is a component of the composition according to the present invention, a metal compound which can generally be used as an oxidizing agent is used, and examples thereof include the metal compounds recited in The Chemistry of the Thiol Group; Part 2, p. 785, (1974).

Specific examples of the above-mentioned metal compounds are metal salts, metal chlorides, and metal oxides comprising uranyl (II), cerium(IV), vanadyl(II), tungsten (VI), palladium (II), platinum (IV), silver (I), silver (II), cadmium (II), mercury (II) or the like, which include uranyl nitrate hexahydrate, cerium (IV) ammonium nitrate, vanadium sulfate, tungsten (VI) oxide, silver nitrate, cadmium (II) sulfate octahydrate, platinum (IV) chloride, mercury (II) chloride, and palladium (II) chloride. Preferable examples are metal salts, metal chlorides, and metal oxides comprising chrome (III), molybdenum (VI), manganese (II), aluminum (III) or the like, which include chrome sulfate/potassium sulfate/24H$_2$O, molybdenum (VI) ammonium oxide tetrahydrate, sodium dihydrate, manganese (II) sulfate tetrahydrate, and manganese dioxide. More preferable are metal salts, metal chlorides, and metal oxides such as iron (II), iron (III), zinc (II), tin (II), nickel (II), cobalt (II), copper (II) or the like, which include iron (II) sulfate heptahydrate, iron (III) octylate, cobalt (II) sulfate heptahydrate, nickel (II) sulfate, copper (II) sulfate pentahydrate, copper (II) chloride dihydrate, zinc (II) sulfate heptahydrate, zinc (II) octylate, zinc oxide, and tin (II) chloride dihydrate. A reason for the above-mentioned metal compounds being preferable is that when used in applications such as coatings, the initial properties of the coating film obtained therefrom are superior.

Here, metal salts include salts of metals and acids, for example, inorganic acids such as nitric acid and sulfuric acid, and organic acids such as octylic acid.

In addition, the above-mentioned metals may be used as metal chelate compounds prepared using known chelating agents. However, metal chelate compounds prepared from chrome (III), molybdenum (VI), manganese (II), aluminum (III) or the like are preferably used, and metal chelate compounds prepared from iron (II), iron (III), zinc (II), tin (II), nickel (II), cobalt (II), copper (II) or the like are even more preferably used. The reason for the above-mentioned metal compounds being preferable is that when used in applications such as coatings, the initial properties of the coating film obtained therefrom are superior. As the known chelating agent, the following can be mentioned as examples; polyaminocarboxylic acids, such as ethylenediaminetetraacetic acid, iminodiacetic acid, nitrotriacetic acid, hydroxyethyliminodiacetic acid, hydroxyethylethylenediaminetriacetic acid, and dihydroxyethylglycine; polyaminophosphoric acids, such as ethylenediamine tetrakis (methylenephosphonic acid), nitrotris (methylenephosphonic acid); and oxycarboxylic acids such as citric acid. In addition, the above-mentioned metal chelate compounds may be used as water-soluble salts of, for example, sodium or potassium, by means of a known method such as the method disclosed in Japanese Unexamined Patent Application, First Publication No. Hei 8-113730.

With regard to the equivalence ratio of the metal compound and the 5-membered ring dithiocarbonate group, with a mixing ratio in which $$\frac{\text{metal compounds}}{\text{5-membered ring dithiocarbonate groups}}$$

is 0.0001 to 10, preferably 0.001 to 3, superior properties can be obtained.

The composition of the present invention comprises a compound or polymer having a dithiocarbonate group, a nucleophile and a metal compound, and is obtained by uniformly dispersing and mixing all of these components. However, depending on the goal and the application, solutions or suspensions in which a solvent has been added to the composition are also suitable. In this situation, as the solvent, for example, the above-mentioned solvents for polymerization can be used alone or as a mixture of 2 to 4 types and can be used in an amount of 0.2 to 100 times (by weight) to the polymer or compound. A composition which contains this type of solvent can be obtained by adding the nucleophile and the metal compound to the polymerization reaction solution as it is, to the concentrated polymerization reaction solution, or to the polymerization reaction solution to which a necessary amount of solvent has been added. Alternatively, it can be obtained by adding the nucleophile, the metal compound, and the solvent to the isolated polymer or compound, and stirring. In addition, the concept of the composition of the present invention includes compositions in which curing has begun through completely cured compositions obtained by the addition of the amino compound and the metal compound to the above-mentioned polymer or compound.

In addition, with regard to the order in which the nucleophile and the metal compound are added to the above-mentioned polymer or compound, either one can be added first.

In addition, with the composition of the present invention, it is possible to obtain a coating film which has superior initial properties due to the promotion of the formation of the disulfide bonds by the above-mentioned metal compound. In addition, the composition of the present invention cures quickly even by drying at room temperature.

The solution or suspension of the composition of the present invention can be used as a clear coating as such, or it can be used as a colored coating by means of the addition of a known pigment or dispersed pigment. The method for dispersing the pigment is not particularly limited and known methods such as those using paint shakers or ball mills can be employed.

With the composition according to the present invention, various ultraviolet absorbers, antioxidants, hindered amine light stabilizers, pigment dispersants, or the like may be incorporated, if necessary. In addition, if necessary, the composition according to the present invention may comprise various conventionally used alkyd resins, acrylic resins, cellulose resins, petroleum resins, epoxy resins, plasticizers, film-forming auxiliaries, or the like.

When the composition according to the present invention is used in a coating, a coating process such as conventional brush coating, spray coating, or the like may be employed, and the curing conditions may be selected from a wide range from room temperature drying to heat drying. The type of article to which the composition is applied can be metal, wood, plastic, inorganic materials, concrete, asphalt, or the like. The composition can be used as any of an under coat, a top coat, or a one-coat finishing.

With the coated article obtained by applying a coating containing the above-mentioned composition to the surface of these articles and allowing it to cure, it is possible to protect a material and to improve the appearance due to the superior properties of the coating film obtained therefrom.

The composition of the present invention can be used by itself as a clear ink, but it can also be used as a colored ink, with a pigment, a dispersed pigment, a toner, dye, or a mixture of these dispersed or dissolved as a mixture of a liquid or a paste. The process of dispersing the pigment is not particularly limited, and a conventional paint shaker, ball mill, or the like can be used. Inks in which the composition of the present invention can be used are, for example, any of relief printing ink, lithographic ink, flexographic ink, and rotogravure ink. The types of printing material are not particularly limited, and examples thereof include paper, paper board, metal plate, metal foil, plastic film, plastic molded products, fiber, and glass.

Since the curing speed of the composition of the present invention is high, it can be suitably used as an adhesive or a sealing agent. For example, it can be used in applications such as adhesion of automobile parts, joining of electronic parts, sealing agents for semiconductors, wrapping materials, laminated wood materials, coating cloths, joining of construction materials, chemical group, space filling agents, insulating agents, or the like.

In the following, embodiments of the present invention will be explained using examples and reference examples.
Reference Example 1: Synthesis of a vinylcopolymer (Resin: A—1)

A flask equipped with a dropping device, a stirrer, a thermometer, a condenser, and a nitrogen gas introduction tube was charged with 150 g of methyl isobutyl ketone (MIBK), and the temperature was raised to 100° C. Then, after purging the flask with nitrogen, a liquid mixture of 7.5 g of 5-(methacryloyl)methyl-1,3-oxathiolane-2-thione, 141 g of butyl methacrylate (BMA), and 1.5 g of 2,2'-azobis-2-methylbutyronitrile (AMBN), as a polymerization catalyst, was added dropwise over 3 hours. The polymerization was completed after aging at 100° C. for 3 hours to yield a resin solution possessing a solid content of 50% by weight and a styrene equivalent weight-average molecular weight of 25,000. The weight-average molecular weight was analyzed by gel permeation chromatography (GPC) in accordance with the following method. In addition, weight-average molecular weights in the following reference examples were measured by a similar method.

Conditions of GPC Analysis
  Column: HXL-L, GMHXL, G-4000HXL, and G-2000HXL (manufactured by Tosoh Corporation) connected serially
  Column retention
  temperature: 40° C.
  Detector: RI
  Eluent: Tetrahydrofuran (flow rate: 1 ml/min)

Reference Example 2 (Resin: A—2)

Tetrahydrofuran (5 L), 500 g of bisphenol A—epichlorohydrin type epoxy resin ("E-1001", manufactured by Yuka Shell Epoxy Kabushiki Kaisha), and 25 g of lithium bromide were added to a 10 L flask equipped with devices similar to those used in Reference Example 1 and a solution was obtained. Then, 340 mL of carbon disulfide was added dropwise to the solution at 25° C. Thereafter, the contents in the flask were heated to 45° C., and the reaction was allowed to proceed for 8 hours. After the reaction, the reaction liquid was concentrated under reduced pressure. To the thus obtained concentrated residue, 5 L of chloroform and 3 L of water were added, and separation of the liquid was performed. To the extracted organic phase, 5 L of a saturated saline solution was added, and separation of the liquid was performed again. The thus obtained organic phase was dehydrated using 300 g of magnesium sulfate, and thereafter chloroform was removed by distillation to yield 445 g of a crude product. A purified product was obtained by purifying 400 g of the crude product by silica gel column chromatography. NMR and IR analytical data on the obtained purified product are shown below.

$^1$H-NMR (CDCl$_3$, δ ppm, 400 MHz):

1.63 (s, 18H), 2.52 (d, J=5.1 Hz, 2H), 3.73 (dd, J=7.1, 12.0 Hz, 2H),
3.78 (dd, J=7.6, 8.0 HZ, 2H), 4.10 (dd, J=5.6, 12.0 Hz, 4H),
4.13 (dd, J=4.6, 8.0 Hz, 4H), 4.25 (dd, J=5.6, 10.3 Hz, 2H),
4.30 (dd, J=5.6, 10.3 Hz, 2H), 4.35 (q, J=5.4 Hz, 2H), 5.42 (m, 2H),
6.81 (dd, J=1.7, 8.8 Hz, 6H), 6.83 (dd, J=2.0, 8.8 Hz, 6H),
7.13 (dd, J=1.5, 8.0 Hz, 12H)
IR (NaCl, cm$^{-1}$): 508, 1184, 1241, 1606, 3037, 3442

EXAMPLE 1

A clear paint (C—1) was prepared by adding 0.2 g of iron (III) octylate (a mineral spirits solution; iron content: 6%) and 0.12 g of dimethyldiaminopropane to 20 g of resin (A—1) obtained in Reference Example 1.

EXAMPLE 2

A clear paint (C—2) was prepared by adding 0.02 g of iron (III) octylate (a mineral spirits solution; iron content: 6%) and 0.12 g of dimethyldiaminopropane to 20 g of resin (A—1) obtained in Reference Example 1.

EXAMPLE 3

A clear paint (C—3) was prepared by adding 0.2 g of iron (III) octylate (a mineral spirits solution; iron content: 6%) and 0.6 g of a commercially available ketimine compound H—2 (manufactured by Yuka Shell Epoxy Kabushiki Kaisha) to 20 g of resin (A—1) obtained in Reference Example 1.

EXAMPLE 4

A clear paint (C—4) was prepared by adding 0.15 g of copper (II) chloride dihydrate and 0.12 g of dimethyldiaminopropane to 20 g of resin (A—1) obtained in Reference Example 1.

EXAMPLE 5

A clear paint (C—5) was prepared by adding 0.15 g of zinc (II) octylate and 0.12 g of dimethyldiaminopropane to 20 g of resin (A—1) obtained in Reference Example 1.

EXAMPLE 6

A clear paint (C—6) was prepared by dissolving 10 g of resin (A—2) obtained in Reference Example 2 in 10 g of tetrahydrofuran (THF), and then adding 0.1 g of iron octylate (a mineral spirits solution; iron content: 6%) and 0.15 g of butylamine.

EXAMPLE 7

A clear paint (C—7) was prepared by dissolving 10 g of resin (A—2) obtained in Reference Example 2 in 10 g of tetrahydrofuran (THF), and then adding 0.1 g of zinc (II) octylate and 0.18 g of dibutylamine.

COMPARATIVE EXAMPLE 1

A clear paint (C—8) was prepared by adding 0.12 g of dimethyldiaminopropane to 20 g of resin (A—1) obtained in Reference Example 1.

COMPARATIVE EXAMPLE 2

A clear paint (C—9) was prepared by dissolving 10 g of resin (A—2) obtained in Reference Example 2 in 10 g of tetrahydrofuran (THF), and then adding 0.15 g of butylamine.

Test Example 1

Test pieces were prepared by applying the clear paints obtained in Examples 1 to 7 and Comparative Examples 1 and 2 to polished steel plates (manufactured by Japan Test Panel), which were treated with iron phosphate, using an applicator coater so that the thickness of the films after drying would be 50 μm, and drying them at room temperature for one day. The following evaluation test was conducted on the test pieces.

Gel fraction: About 0.5 g of the film was collected from a test piece, and cleaned by a Soxhlet extractor under acetone reflux for 8 hours. Then, drying under reduced pressure was performed overnight, and the remaining rate by weight was determined, and was taken as the gel fraction.

The results of Test Example 1 are shown in Tables 1 and 2.

TABLE 1

| Clear Paint | Examples 1 to 7 | | | | | | |
|---|---|---|---|---|---|---|---|
|  | C - 1 | C - 2 | C - 3 | C - 4 | C - 5 | C - 6 | C - 7 |
| Gel Fraction | 81% | 83% | 73% | 79% | 95% | 88% | 80% |

TABLE 2

|  | Comparative Examples 1 to 2 | |
|---|---|---|
| Clear Paint | C-8 | C-9 |
| Gel Fraction | 67% | 71% |

From Tables 1 and 2, it can be understood that the compositions of the present invention have a high curing rate, and the coating films obtained therefrom are superior in their initial properties.

INDUSTRIAL APPLICABILITY

According to the present invention, a composition comprising a compound having at least one 5-membered ring dithiocarbonate group; a nucleophile; and a metal compound is provided which is useful in applications such as coatings, adhesives, inks, sealing agents, or the like.

What is claimed is:

1. A composition comprising a compound having at least one 5-membered ring dithiocarbonate group represented by formula (I):

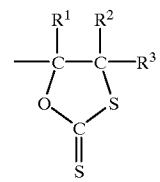

wherein, $R^1$, $R^2$ and $R^3$ independently represent hydrogen or lower alkyl, (2) a nucleophile, and (3) a metal compound selected from the group consisting of a metal salt, a metal chloride, a metal oxide and a metal chelate compound.

2. The composition according to claim 1, wherein said compound having at least one 5-membered ring dithiocarbonate group is a polymer containing a structural unit having a 5-membered ring dithiocarbonate group.

3. The composition according to claim 2, wherein said compound having at least one 5-membered ring dithiocarbonate group is a copolymer comprising structural units having a 5-membered ring dithiocarbonate group and structural units which do not have a 5-membered ring dithiocarbonate group.

4. The composition according to claim 3, wherein said copolymer is a vinyl copolymer.

5. The composition according to claim 4, wherein the vinyl copolymer contains a structural unit represented by general formula (II)

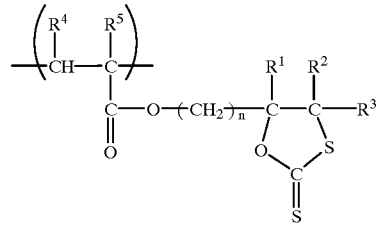

(in general formula (II), $R^1$, $R^2$, and $R^3$ are the same or different and each of which represents hydrogen or lower alkyl; $R^4$ and $R^5$ are the same or different and each of which represents hydrogen, methyl, or ethyl; and n represents an integer of 1 to 4).

6. The composition according to claim 5, wherein the vinyl copolymer is a copolymer comprising the structural units represented by general formula (II) and acrylic acid, methacrylic acid or a lower alkyl ester thereof.

7. The composition according to claim 1, wherein the compound having at least one 5-membered ring dithiocarbonate group is a compound represented by general formula (III):

$$\underset{\underset{\substack{|| \\ S}}{\overset{\overset{S \diagup \diagdown O}{\diagdown C \diagup}}{}}}{CH_2\text{-}CH\text{-}CH_2} \text{---} \left[ O \text{---} R^6 \text{---} R^7 \text{---} R^6 \text{---} O \text{---} CH_2 \text{---} \underset{\underset{OH}{|}}{CH} \text{---} CH_2 \right]_m \text{---} O \text{---} R^6 \text{---} R^7 \text{---} R^6 \text{---} O \text{---} \underset{\underset{\substack{|| \\ S}}{\overset{\overset{O \diagup \diagdown S}{\diagdown C \diagup}}{}}}{CH_2\text{---}CH\text{---}CH_2} \qquad (III)$$

(wherein $R^6$ represents phenylene in which 1 to 4 hydrogen atoms may be substituted by Br, or cyclohexylene; $R^7$ represents methylene, $C(CH_3)_2$, or S; and m represents an integer of 1 to 40).

8. The composition according to one of claims 1 to 7, wherein said nucleophile is an amino compound, or a ketimine derivative, an enamine derivative or an aldimine derivative thereof.

9. The composition according to claim 1, wherein said metal compound is a metal salt, a metal chloride, a metal oxide, or a metal chelate compound comprising uranyl (II), cerium (IV), vanadyl (II), tungsten (VI), palladium (II), platinum (IV), silver (I), silver (II), cadmium (II), mercury (II), chrome (III), molybdenum (VI), manganese (II), aluminum (III), iron (II), iron (III), zinc (II), tin (II), nickel (II), cobalt (II), or copper (II).

10. The composition according to claim 1, wherein said metal compound is a metal salt, a metal chloride, a metal oxide, or a metal chelate compound of chrome (III), molybdenum (VI), manganese (II), aluminum (III), iron (II), iron (III), zinc (II), tin (II), nickel (II), cobalt (II), or copper (II).

11. The composition according to claim 1, wherein said metal compound is a metal salt, a metal chloride, or a metal oxide, or a metal chelate compound of iron (II), iron (III), zinc (II), tin (II), nickel (II), cobalt (II), or copper (II).

12. A coating containing the composition according to one of claims 1 to 8.

13. A coated article obtained by applying the coating according to claim 13 to a surface of an article and allowing said coating to cure.

14. An ink containing the composition according to one of claims 1 to 8.

15. An adhesive containing the composition according to one of claims 1 to 8.

16. A sealing agent containing the composition according to one of claims 1 to 8.

17. The composition according to one of claims 1 to 8 and 10 to 12, wherein the equivalence ratio of the metal compound to the 5-membered ring dithiocarbonate group is 0.0001 to 10.

18. The composition according to one of claims 1 to 8 and 10 to 12, wherein the equivalence ratio of the metal compound to the 5-membered ring dithiocarbonate group is 0.001 to 3.

19. A coating containing the composition according to claim 18.

20. A coated article obtained by applying the coating according to claim 20 to a surface of an article and allowing said coating to cure.

21. A coating containing the composition according to claim 19.

22. A coated article obtained by applying the coating according to claim 22 to a surface of an article and allowing said coating to cure.

* * * * *

UNITED STATES PATENT AND TRADEMARK OFFICE
CERTIFICATE OF CORRECTION

PATENT NO. : 6,160,044
DATED : December 12, 2000
INVENTOR(S) : Shinichiro Jimbo et al.

It is certified that error appears in the above-identified patent and that said Letters Patent is hereby corrected as shown below:

Column 11,
Line 14, "group," should read -- grout, --.

Column 15,
Line 38, "claims 1 to 8." should read -- claims 1 to 11. --.

Column 16,
Line 13, "claim 13" should read -- claim 12 --;
Lines 16, 18 and 19, "claims 1 to 8." should read -- claims 1 to 11. --;
Line 20, "claims 1 to 8 and" should read -- claims 1 to 11, --;
Line 21, "10 to 12," should be deleted;
Line 24, "claims 1 to 8 and" should read -- claims 1 to 11, --;
Line 25, "10 to 12," should be deleted;
Line 29, "claim 18." should read -- claim 17. --;
Line 31, "claim 20" should read -- claim 19 --;
Line 34, "claim 19." should read -- claim 18. --; and
Line 36, "claim 22" should read -- claim 21 --.

Signed and Sealed this

Eleventh Day of June, 2002

Attest:

*Attesting Officer*

JAMES E. ROGAN
*Director of the United States Patent and Trademark Office*